US010413844B2

(12) United States Patent
Hoke, II et al.

(10) Patent No.: US 10,413,844 B2
(45) Date of Patent: *Sep. 17, 2019

(54) LIQUID-LIQUID EXTRACTION COMPOSITION USEFUL IN PROCESSING WATER-SOLUBLE SURFACTANTS

(75) Inventors: Steven Hamilton Hoke, II, West Chester, OH (US); John Christian Haught, West Chester, OH (US); Marc Alan Hester, Cincinnati, OH (US); Brian David Clair, Ft. Wright, KY (US)

(73) Assignee: THE PROCTER & GAMBLE COMPANY, Cincinnati, OH (US)

( * ) Notice: Subject to any disclaimer, the term of this patent is extended or adjusted under 35 U.S.C. 154(b) by 999 days.

This patent is subject to a terminal disclaimer.

(21) Appl. No.: 13/564,841

(22) Filed: Aug. 2, 2012

(65) Prior Publication Data

US 2013/0032748 A1   Feb. 7, 2013

Related U.S. Application Data

(60) Provisional application No. 61/514,203, filed on Aug. 2, 2011.

(51) Int. Cl.
| | | |
|---|---|---|
| *B01D 11/04* | (2006.01) | |
| *B01F 17/00* | (2006.01) | |
| *A61K 8/44* | (2006.01) | |
| *A61K 8/03* | (2006.01) | |
| *A61K 8/41* | (2006.01) | |
| *A23L 29/10* | (2016.01) | |

(52) U.S. Cl.
CPC .......... *B01D 11/0407* (2013.01); *A23L 29/10* (2016.08); *A61K 8/03* (2013.01); *A61K 8/41* (2013.01); *A61K 8/44* (2013.01); *B01F 17/00* (2013.01)

(58) Field of Classification Search
CPC ... B01D 11/0407; C01B 25/46; C01B 25/465; A61K 8/44; A61K 8/41; A61K 8/03; A61K 8/55; A61K 8/556; A61K 8/463; A23L 29/10; B01L 17/00; B01L 17/0042; B01L 17/0057; B01L 17/0064; B01L 17/0085
USPC .............. 516/141, 186, 198, 199, 200, 203; 210/634, 642, 643, 644, 648; 424/57; 558/208, 146; 426/654
See application file for complete search history.

(56) References Cited

U.S. PATENT DOCUMENTS

| | | | | |
|---|---|---|---|---|
| 2,199,398 | A * | 5/1940 | Engelmann | C07C 303/24 558/31 |
| 2,610,195 | A * | 9/1952 | Gebhart | 552/545 |
| 2,818,421 | A * | 12/1957 | Max | C07F 9/025 558/150 |
| 3,215,741 | A * | 11/1965 | Chadwick | C07C 291/04 422/224 |
| 3,275,673 | A * | 9/1966 | Barlow | C07C 291/04 510/503 |
| 3,470,270 | A * | 9/1969 | Wardi | C07F 9/08 252/396 |
| 3,748,324 | A * | 7/1973 | Mizutani Etal | 536/119 |
| 4,096,175 | A * | 6/1978 | Naylor et al. | 562/42 |
| 4,117,108 | A * | 9/1978 | Shapiro | A61Q 11/00 424/49 |
| 4,175,092 | A * | 11/1979 | Bakker et al. | 558/41 |
| 4,352,829 | A | 10/1982 | Noyes et al. | |
| 4,670,575 | A * | 6/1987 | Kurosaki | C07F 9/09 558/110 |
| 5,075,498 | A * | 12/1991 | Perine | C07C 227/08 562/553 |
| 5,075,501 | A * | 12/1991 | Borland | C11D 1/75 564/297 |

(Continued)

FOREIGN PATENT DOCUMENTS

| | | |
|---|---|---|
| FR | 2 733 982 A1 | 11/1996 |
| JP | H05111920 | 5/1993 |

(Continued)

OTHER PUBLICATIONS

Nelson et al., The Preparation of Long-chain Monoalkyl Phosphates from Pyrophosphoric Acid and Alcohols, Inorganic Chemistry, vol. 2, No. 4, Aug. 1963, pp. 775-778.*
Aissou et al., "Limonene as an agro-chemical building block for the synthesis and extraction of bioactive compounds," C. R. Chimie 20 (2017) 346-358 (Available online Jun. 28, 2016).*
International Search Report for PCT/US2012/049332, dated Nov. 22, 2012.
International Search Report for PCT/US2012/049314, dated Dec. 10, 2012.

* cited by examiner

*Primary Examiner* — Stephen E Rieth
(74) *Attorney, Agent, or Firm* — James E. Oehlenschlager; Jason J Camp

(57) ABSTRACT

Compositions useful in liquid-liquid extraction processes for improving the taste of water-soluble surfactants, said composition comprising: from about 5% to about 60%, by weight of the composition, of water soluble surfactant; from about 10% to about 90%, by weight of the composition, of water; from about 10% to about 90%, by weight of the composition, of extraction solvent; at least 0.01%, by weight of the composition, of undesirable non-polar materials; wherein the extraction solvent is selected from solvents having individual Hansen solubility parameters of a dispersion force component ($\delta_D$) ranging from about 15 to about 17 $(MPa)^{0.5}$, a polar component ($\delta_P$) ranging from 0 to about 9 $(MPa)^{0.5}$ and a hydrogen bonding component ($\delta_H$) ranging from 0 to about 11 $(MPa)^{0.5}$.

20 Claims, No Drawings

(56) References Cited

U.S. PATENT DOCUMENTS

| | | | | |
|---|---|---|---|---|
| 5,130,488 | A * | 7/1992 | Smith | C11D 1/75 564/297 |
| 5,245,070 | A * | 9/1993 | Nishikawa | B01F 17/0064 106/2 |
| 5,322,643 | A | 6/1994 | Schwartz et al. | |
| 5,371,250 | A * | 12/1994 | Seitz | C07C 231/12 554/41 |
| 5,432,268 | A * | 7/1995 | Borsotti et al. | 536/18.5 |
| 5,756,543 | A * | 5/1998 | Katsuragi | A21D 2/16 514/547 |
| 5,807,516 | A | 9/1998 | Cottrell et al. | |
| 5,807,816 | A | 9/1998 | Cottrell et al. | |
| 5,840,676 | A * | 11/1998 | Drapier | C11D 17/0021 510/277 |
| 5,922,897 | A * | 7/1999 | Hu | C07F 9/091 558/122 |
| 8,697,036 | B2 * | 4/2014 | Hoke et al. | 424/49 |
| 8,865,192 | B2 * | 10/2014 | Swaine, Jr. | A61K 8/4973 424/401 |
| 9,072,671 | B2 * | 7/2015 | Hoke, II | A61K 8/18 |
| 9,078,826 | B2 * | 7/2015 | Hoke, II | A61K 8/44 |
| 2002/0010104 | A1 | 1/2002 | Ewbank et al. | |
| 2007/0123445 | A1 | 5/2007 | Tuzi et al. | |
| 2008/0247973 | A1 * | 10/2008 | Baig et al. | 424/57 |
| 2009/0069573 | A1 * | 3/2009 | Pieter | C09B 67/0096 548/427 |
| 2010/0069477 | A1 | 3/2010 | Itoh et al. | |
| 2012/0078008 | A1 * | 3/2012 | Daugs | 562/101 |
| 2013/0034506 | A1 * | 2/2013 | Hoke et al. | 424/48 |
| 2013/0034508 | A1 * | 2/2013 | Hoke et al. | 424/57 |
| 2014/0037555 | A1 * | 2/2014 | Hoke, II | A61K 8/18 424/52 |
| 2014/0054223 | A1 * | 2/2014 | Smit et al. | 210/638 |
| 2014/0105833 | A1 * | 4/2014 | Hoke et al. | 424/57 |
| 2015/0265515 | A1 * | 9/2015 | Hoke, II | A61K 8/44 424/57 |
| 2015/0265521 | A1 * | 9/2015 | Hoke, II | A61K 8/18 424/52 |

FOREIGN PATENT DOCUMENTS

| | | |
|---|---|---|
| JP | H06319973 | 11/1994 |
| JP | H11140486 | 5/1999 |
| JP | H11171746 | 6/1999 |
| JP | H11279117 | 10/1999 |
| WO | WO1994/09108 A1 | 4/1994 |
| WO | WO 1998/26036 A1 | 6/1998 |
| WO | WO 2000/06690 A1 | 2/2000 |
| WO | WO 2008/005550 A2 | 1/2008 |

LIQUID-LIQUID EXTRACTION COMPOSITION USEFUL IN PROCESSING WATER-SOLUBLE SURFACTANTS

CROSS REFERENCE TO RELATED APPLICATION

This Application claims priority to U.S. Provisional Application No. 61/514,203, filed Aug. 2, 2011, which is incorporated herein by reference.

FIELD OF THE INVENTION

The present invention relates to compositions containing water-soluble surfactants, undesirable non-polar materials, extraction solvent and water. The present invention further relates to use of such compositions in liquid-liquid extraction processes for improving the taste and/or odor of water-soluble surfactants.

BACKGROUND OF THE INVENTION

Traditionally, much effort has been expended to improve the taste, color, odor or clarity of oral care compositions such as dentifrice (toothpaste), mouth rinse, and the like. Because of the nature of such compositions, the taste of a product may often be of more importance to consumers than the actual or perceived efficacy. Since many efficacious oral care components have undesirable taste, color, odor or clarity, efforts to improve these characteristics are common in the art. For taste, one way to remedy an undesirable product taste is to add additional components, such as flavors, that will improve the overall taste experience for the consumer. However, such remedies can be expensive and it may be difficult to entirely mask an undesirable taste. Improvement of color or clarity through dyes or other additives has similar issues.

Water-soluble surfactants such as alkyl phosphate surfactants are commercially available for use in a variety of consumer products, including oral care compositions. These anionic surface active organophosphate agents have a strong affinity for enamel surface and have sufficient surface binding propensity to desorb pellicle proteins and remain affixed to enamel surfaces. Such properties make these materials desirable for incorporation in oral care compositions such as toothpaste. However, these materials have not been widely commercialized in oral care compositions, despite their desirable properties. One reason for this lack of commercialization may be the negative taste and/or odor profile commonly associated with commercially available alkyl phosphate materials. Although taste may not be a consideration in other consumer product industries, such as laundry, shampoo or personal cleansing, it is an important consideration in oral care. Similarly, while any undesirable odor associated with materials used in laundry, shampoo or personal cleansing products can typically be remedied by the addition of perfume, perfume levels must be kept to a minimum in oral care compositions for consumer acceptance and could produce further unpleasant tastes when utilized.

Purification of surfactant materials through steam-stripping, vacuum-stripping, and/or carbon filtration processes is also generally known to beneficially remove impurities to increase efficacy, minimize undesirable side reactions, and the like. However, these purification processes have been found to be insufficient to remedy the unpleasant tastes and/or odors associated with commercially available water-soluble surfactant materials.

Liquid/liquid extractions (LLE) are generally known in the art as useful for separating components of a mixture, wherein the constituents have differing polarities which can be separated when mixed within two immiscible solvents that form a liquid bilayer after mixing. For example, LLEs are useful for purifying or cleaning samples which contain impurities of significantly differing polarity than the majority or desirable component(s) of the sample. This can be achieved by mixing a sample with a solvent that is immiscible with the primary liquid in which the sample is dissolved.

LLE has been utilized in chemical processing to reduce or eliminate undesirable by-products or contaminants. For instance, PCT Patent Application WO 2008005550 to Hoke, et al (Procter & Gamble) discloses a water washing procedure to remove polar sulfur impurities from peppermint oils to avoid malodor formation when formulated in dentifrice containing stannous ions. In U.S. Pat. No. 4,352,829 to Noyes, et al (Procter & Gamble) an ethyl acetate extraction of caffeine from coffee was shown to be an effective decaffeination process.

However, there is still an interest in finding ways to improve the overall taste and/or odor of water-soluble surfactants such as those used in an oral care composition that are efficacious, cost-effective, and desirable to consumers.

SUMMARY OF THE INVENTION

It has now surprisingly been found that liquid-liquid extraction processes utilizing solvents such as ethyl acetate may be useful to significantly reduce the occurrence of non-polar materials found in water-soluble surfactant raw materials and thereby improve the surfactant's odor and/or taste profile.

Without being limited by theory, it is now believed that water-soluble surfactants previously generally thought to have bad taste and/or odor profiles stemming from the pure material itself are in fact surprisingly acceptable in terms of taste and odor. It has been surprisingly found that non-polar materials commonly present in commercially available water-soluble surfactant compositions such as residual alcohols, alcohol ethoxylates, aldehydes, ethers, ketones, alkylamines, and esters, may be linked to the majority of the negative taste and odor profiles previously associated with the surfactants themselves. Since some of these materials are often used in flavors and perfumes, it was further surprising that a new process for more efficiently extracting these materials from the underlying surfactant would produce such results. For example, dodecanol and dodecanal are commonly taught to be safe and useful for inclusion in flavors and perfumes, yet it has been surprisingly found that if included in water-soluble surfactant compositions at significantly higher levels, these materials present an unpleasant taste such as bitter, soapy and the like.

Further without being limited by theory, liquid-liquid extraction using the appropriate solvent is more effective than previously known techniques to purify such surfactants, allowing for the incorporation of such surfactants into oral care products with minimal negative taste and/or odor attributes.

The present invention is therefore directed to compositions useful in such liquid-liquid extraction processes for improving the taste of water-soluble surfactants, said composition comprising: from about 5% to about 60%, by weight of the composition, of water soluble surfactant; from about 10% to about 90%, by weight of the composition, of water; from about 10% to about 90%, by weight of the composition, of extraction solvent; and at least 0.01%, by weight of the composition, of at least one undesirable non-polar material; wherein the extraction solvent is selected from solvents having individual Hansen solubility parameters of a dispersion force component ($\delta_D$) ranging from about 15 to about 17 $(MPa)^{0.5}$, a polar component ($\delta_P$) ranging from 0 to about 9 $(MPa)^{0.5}$ and a hydrogen bonding component ($\delta_H$) ranging from 0 to about 11 $(MPa)^{0.5}$.

In another embodiment, the present invention relates to a composition useful in liquid-liquid extraction processes for improving the taste of water-soluble surfactants, said composition consisting essentially of: from about 30% to about 60% of a water soluble surfactant; from about 20% to about 80% water; from about 20% to about 80% of ethyl acetate; from about 0.01% to about 20%, by weight of the composition, of undesirable non-polar materials.

In another embodiment, the present invention relates to compositions as set forth above wherein the composition comprises an aqueous phase and a solvent phase.

In another embodiment, the present invention relates to compositions as set forth above wherein the aqueous phase comprises the water soluble surfactant and water.

In another embodiment, the present invention relates to compositions as set forth above wherein the solvent phase comprises the extraction solvent and at least one undesirable non-polar material.

In another embodiment, the present invention relates to compositions as set forth above wherein the water-soluble surfactant is at least about 20% soluble in water.

In another embodiment, the present invention relates to compositions as set forth above wherein the water-soluble surfactant is selected from anionic surfactants, zwitterionic surfactants and mixtures thereof and is at least about 30% soluble in water.

In another embodiment, the present invention relates to compositions as set forth above wherein the water soluble surfactant is selected from alkyl phosphate surfactants, alkyl phosphate ethoxylated surfactants, lauryl sulfate surfactants, betaine surfactants, amine oxide surfactants, and mixtures thereof.

In another embodiment, the present invention relates to compositions as set forth above wherein the water-soluble surfactant is selected from cocoamidopropyl betaines, lauryl betaines capryl/capramidobetaines, sodium lauryl sulfates, mono alkyl phosphates, alkyl ethoxylated phosphates, amine oxides, and mixtures thereof.

In another embodiment, the present invention relates to compositions as set forth above wherein the water soluble surfactant is a mono alkyl phosphate surfactant.

In another embodiment, the present invention relates to compositions as set forth above wherein the extraction solvent has individual Hansen solubility parameters of a dispersion force component ($\delta_D$) ranging from about 13 to about 19 $(MPa)^{0.5}$, a polar component ($\delta_P$) ranging from about 2 to about 9 $(MPa)^{0.5}$ and a hydrogen bonding component ($\delta_H$) ranging from about 2 to about 11 $(MPa)^{0.5}$.

In another embodiment, the present invention relates to compositions as set forth above wherein the extraction solvent is selected from ethyl acetate, water-saturated ethyl acetate, ethyl propionate, ethyl butyrate, ethyl pentanoate, ethyl caproate, ethyl caprylate, ethyl pelargonate methyl acetate, methyl propionate, methyl butyrate, short chain esters and mixtures thereof.

In another embodiment, the present invention relates to compositions as set forth above wherein the extraction solvent is ethyl acetate.

In another embodiment, the present invention relates to compositions as set forth above wherein the extraction solvent is selected from food grade ethyl esters.

In another embodiment, the present invention relates to compositions as set forth above wherein the ratio of extraction solvent to water soluble surfactant in the extraction mixture is from about 1:10 to about 10:1.

In another embodiment, the present invention relates to compositions as set forth above wherein the ratio of extraction solvent to water soluble surfactant in the extraction mixture is from about 1:2 to about 2:1.

In another embodiment, the present invention relates to compositions as set forth above wherein the composition further comprises a phase separation enhancer selected from salt, pH modifiers, and mixtures thereof.

In another embodiment, the present invention relates to use of the compositions set forth above in a liquid-liquid extraction process.

DETAILED DESCRIPTION OF THE INVENTION

The present invention relates to compositions which may be used in processes for improving the taste of water-soluble surfactants using liquid-liquid solvent extraction. Such compositions include:
a. from about 5% to about 60%, by weight of the composition, of water soluble surfactant;
b. from about 10% to about 90%, by weight of the composition, of water;
c. from about 10% to about 90%, by weight of the composition, of extraction solvent;
d. at least 0.01%, by weight of the composition, of undesirable non-polar materials;
wherein the extraction solvent is selected from solvents having individual Hansen solubility parameters of a dispersion force component ($\delta_D$) ranging from about 15 to about 17 $(MPa)^{0.5}$, a polar component ($\delta_P$) ranging from 0 to about 9 $(MPa)^{0.5}$ and a hydrogen bonding component ($\delta_H$) ranging from 0 to about 11 $(MPa)^{0.5}$.

These elements will be discussed in more detail below.

Water Soluble Surfactant

The compositions of the present invention contain from about 5% to about 60%, by weight of the composition of a water-soluble surfactant. In one embodiment, the compositions of the present invention contain from about 10% to about 50%, alternatively from about 20% to about 30%, by weight of the composition, of a water-soluble surfactant.

As used herein "water-soluble surfactant" refers to those surfactants that are at least partially soluble in water, when measured at room temperature (25° C.). In one embodiment, the water-soluble surfactant is at least 10% soluble in water, alternatively is at least 20% soluble in water, and still alternatively is at least 30% soluble in water, alternatively at least 40% soluble in water.

Examples of water-soluble surfactants that may be purified by the processes herein include cocoamidopropyl betaines, lauryl betaines, capryl/capramidobetaines, sodium lauryl sulfates, mono alkyl phosphates, alkyl ethoxylated phosphates, amine oxides, and mixtures thereof.

Water-soluble surfactants useful herein may, in some embodiments be selected from anionic surfactants such as alkyl phosphates. These surface active organophosphate agents have a strong affinity for enamel surface and have sufficient surface binding propensity to desorb pellicle proteins and remain affixed to enamel surfaces. Suitable examples of organophosphate compounds include mono-, di- or triesters represented by the general structure below wherein Z1, Z2, or Z3 may be identical or different, at least one being an organic moiety, in one embodiment selected from linear or branched, alkyl or alkenyl group of from 1 to 22 carbon atoms, optionally substituted by one or more phosphate groups; alkoxylated alkyl or alkenyl, (poly)saccharide, polyol or polyether group.

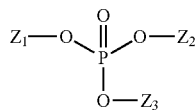

Some other agents include alkyl or alkenyl phosphate esters represented by the following structure:

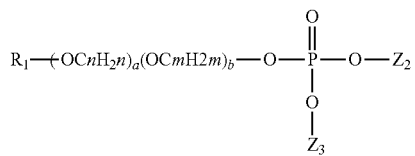

wherein R1 represents a linear or branched, alkyl or alkenyl group of from 6 to 22 carbon atoms, optionally substituted by one or more phosphate groups; n and m, are individually and separately, 2 to 4, and a and b, individually and separately, are 0 to 20; Z2 and Z3 may be identical or different, each represents hydrogen, alkali metal, ammonium, protonated alkyl amine or protonated functional alkyl amine such as an alkanolamine, or a R1—(OCnH2n)a(OCmH2m)b-group. Examples of suitable agents include alkyl and alkyl (poly)alkoxy phosphates such as lauryl phosphate; PPG5 ceteareth-10 phosphate; Laureth-1 phosphate; Laureth-3 phosphate; Laureth-9 phosphate; Trilaureth-4 phosphate; C12-18 PEG 9 phosphate; Sodium dilaureth-10 phosphate. In one embodiment, the alkyl phosphate is polymeric. Examples of polymeric alkyl phosphates include those containing repeating alkoxy groups as the polymeric portion, in particular 3 or more ethoxy, propoxy isopropoxy or butoxy groups.

Zwitterionic or amphoteric surfactants useful in the present invention include derivatives of aliphatic quaternary ammonium, phosphonium, and sulfonium compounds, in which the aliphatic radicals can be straight chain or branched, and wherein one of the aliphatic substituents contains from about 8 to 18 carbon atoms and one contains an anionic water-solubilizing group, e.g., carboxy, sulfonate, sulfate, phosphate or phosphonate. Suitable amphoteric surfactants include betaine surfactants such as disclosed in U.S. Pat. No. 5,180,577 to Polefka et al. Typical alkyl dimethyl betaines include decyl betaine or 2-(N-decyl-N,N-dimethylammonio)acetate, coco betaine or 2-(N-coco-N,N-dimethyl ammonio)acetate, myristyl betaine, palmityl betaine, lauryl betaine, cetyl betaine, stearyl betaine, etc. The amidobetaines are exemplified by cocoamidoethyl betaine, cocoamidopropyl betaine (CAPB), and lauramidopropyl betaine. The unwanted tastes often associated with these surfactants are soapy, bitter, chemical, and/or artificial.

Additional suitable polymeric organophosphate agents include dextran phosphate, polyglucoside phosphate, alkyl polyglucoside phosphate, polyglyceryl phosphate, alkyl polyglyceryl phosphate, polyether phosphates and alkoxylated polyol phosphates. Some specific examples are PEG phosphate, PPG phosphate, alkyl PPG phosphate, PEG/PPG phosphate, alkyl PEG/PPG phosphate, PEG/PPG/PEG phosphate, dipropylene glycol phosphate, PEG glyceryl phosphate, PBG (polybutylene glycol)phosphate, PEG cyclodextrin phosphate, PEG sorbitan phosphate, PEG alkyl sorbitan phosphate, and PEG methyl glucoside phosphate. Suitable non-polymeric phosphates include alkyl mono glyceride phosphate, alkyl sorbitan phosphate, alkyl methyl glucoside phosphate, alkyl sucrose phosphates. The unwanted tastes often associated with these surfactants are soapy, chemical, and/or artificial.

Water-soluble amphoteric surfactants useful herein further include amine oxide surfactants Amine oxides are the result of oxidation of tertiary amines, typically C12-C18 alkyl dimethyl, N-oxides. For example, amine oxide surfactants useful herein may include lauryl dimethyl amine oxide; lauryl dihydroxyethyl amine oxide; cocamidopropyl amine oxide; Lauramidopropylamine oxide; cetyl dimethyl amine oxide; 3-Lauramidopropyl-N,N-dimethylamine oxide.

Water-soluble cationic surfactants useful in the present invention include derivatives of quaternary ammonium compounds having one long alkyl chain containing from about 8 to 18 carbon atoms such as lauryl trimethylammonium chloride; cetyl pyridinium chloride; cetyl trimethylammonium bromide; coconut alkyltrimethylammonium nitrite; cetyl pyridinium fluoride; etc. Preferred compounds are the quaternary ammonium halides having detergent properties described in U.S. Pat. No. 3,535,421 to Briner et al. Certain cationic surfactants can also act as germicides in the oral care compositions disclosed herein.

In another embodiment, the water-soluble surfactant is selected from anionic surfactants, zwitterionic surfactants, amphoteric surfactants, cationic surfactants, nonionic surfactants and mixtures thereof. In one embodiment, the water-soluble surfactant is selected from alkyl phosphate surfactants, alkyl phosphate ethoxylated surfactants, lauryl sulfate surfactants, betaine surfactants, betaine ethoxylated surfactants, amine oxide surfactants and mixtures thereof. In another embodiment, the water-soluble surfactant is selected from alkyl phosphate surfactants, alkyl phosphate ethoxylated surfactants, and mixtures thereof. In one embodiment, the water-soluble surfactant is a mono alkyl phosphate surfactant.

In one embodiment, the surfactant is selected from cocoamidopropyl betaines, alkyl ethoxylated phosphates, mono alkyl phosphates, and mixtures thereof.

Water

The compositions of the present invention contain from about 10% to about 90%, by weight of the composition, of water. In one embodiment, the composition contains from about 30% to about 90%, by weight of the composition, of water. In one embodiment, the compositions of the present invention contain from about 50% to about 90%, alternatively from about 50% to about 70%, by weight of the composition, of water.

Extraction Solvent

The compositions herein contain from about 10% to about 90%, by weight of the composition, of extraction solvent. In one embodiment, the composition contains from about 20% to about 80% of the extraction solvent, alternatively from about 30% to about 70%, by weight of the composition, of the extraction solvent.

As used herein, "extraction solvent" refers to any liquid or supercritical fluid that can be used to solubilize undesirable non-polar materials that are contained within a water-soluble surfactant composition. Organic solvents with acceptable safety profiles that will form a liquid bilayer with aqueous surfactants could be used either alone or in combination with other solvents such as ethyl acetate, ethanol, propylene glycol, PEGs, other ethers or esters, or other solvents, etc. to achieve a similar result. One example of a useful supercritical fluid is carbon dioxide.

Extraction solvents useful herein include those having individual Hansen solubility parameters of a dispersion force component ($\delta_D$) ranging from about 15 to about 17 $(MPa)^{0.5}$, a polar component ($\delta_P$) ranging from 0 to about 9 $(MPa)^{0.5}$ and a hydrogen bonding component ($\delta_H$) ranging from 0 to about 11 $(MPa)^{0.5}$.

In one embodiment, the solvent has individual Hansen solubility parameters of a dispersion force component ($\delta_D$) ranging from about 13 to about 19 $(MPa)^{0.5}$, a polar component ($\delta_P$) ranging from about 2 to about 9 $(MPa)^{0.5}$ and a hydrogen bonding component ($\delta_H$) ranging from about 2 to about 11 $(MPa)^{0.5}$. In one embodiment, the polar component ranges from about 4 to about 6, in another embodiment, the hydrogen bonding component ranges from about 6 to about 9.

In addition to Hansen solubility parameters, the solvent will form distinct layers when combined with water and the water-soluble surfactant. In order to quickly determine whether a solvent will meet this criteria, the following visual separation test may be used: using a 30 ml glass vial, add 10 mL of the proposed extraction solvent, 10 mL of a 30% aqueous solution of the water-soluble surfactant composition, cap the vial, shake vigorously for 30 seconds, allow to rest for 30 minutes, visually inspect for visible precipitation and two distinct aqueous layers. If there is no visible precipitation and at least two distinct layers are formed, the solvent passes the visual separation test and may be used as an extraction solvent according to the processes set forth herein.

In one embodiment, the extraction solvents useful herein have a log P value of greater than 0.5.

Extraction solvents useful herein include ethyl acetate, water-saturated ethyl acetate, ethyl propionate, ethyl butyrate, ethyl pentanoate, ethyl caproate, ethyl caprylate, ethyl pelargonate methyl acetate, methyl propionate, methyl butyrate, short chain esters and mixtures thereof. In one embodiment, the extraction solvent is selected from food grade ethyl esters.

In one embodiment, the extraction solvent is substantially free of (i.e. comprises no reasonably measurable quantity of) ethyl lactate, alternatively contains less than 0.0001% of ethyl lactate.

Other extraction solvents useful herein include ketones such as methyl ethyl ketone, ethers such as di-n-propyl ether, lactones, acetals, and mixtures thereof.

Other extraction solvents useful herein include those selected from hexane, cyclohexane, heptane, chloroform, toluene, methylene chloride, methyl nonafluoroether, ethyl nonafluoroether, carbon tetrachloride, and mixtures thereof. HFE 7100, HFE 7200, and HFE 7500 are tradenames of commercially available hydrofluoroethers available from TCI AMERICA, 9211 N. Harborgate Street, Portland, Oreg. 97203, U.S.A.

Mixtures of extraction solvents may also be used.

In one embodiment, the extraction mixture is substantially free of (i.e. comprises no reasonably measurable quantity of) THF.

In one embodiment, the extraction mixture comprises mono alkyl phosphate and is substantially free of (i.e. comprises no reasonably measurable quantity of) 1-octanol and phenoxy ethanol.

Extraction solvents useful herein also include supercritical fluids such as carbon dioxide. As used herein, "supercritical carbon dioxide" is carbon dioxide that is at a temperature and a pressure greater than Tr=1 and Pr=1 Tr is T/Tc where T is the present temperature of the supercritical carbon dioxide and Tc is the critical temperature. Pr is P/Pc where P is the present pressure of the supercritical carbon dioxide and Pc is the critical pressure. Tc, the critical temperature for carbon dioxide ($CO_2$), is 31.1 degrees Celsius (deg. C.), or 304.1 degrees Kelvin (K), and Pc is 73 atmospheres (atm) or about 1073 pounds per square inch (PSI).

In more general terms, supercritical carbon dioxide refers to carbon dioxide that is in a fluid state while also being at or above both its critical temperature and pressure. Carbon dioxide usually behaves as a gas in air at standard temperature and pressure (STP) or as a solid called dry ice when frozen. If the temperature and pressure are both increased from standard temperature and pressure to be at or above the critical point for carbon dioxide, it can adopt properties midway between a gas and a liquid. More specifically, it behaves as a supercritical fluid above its critical temperature (31.1 deg. C.) and critical pressure (73 atm), expanding to fill its container like a gas but with a density like that of a liquid. The supercritical fluid region of the phase diagram is defined as a temperature above the critical temperature (31.1 deg. C.) to a pressure above the critical pressure (73.8 bar or 1070 PSI).

When using a supercritical fluid as the extraction solvent, it is possible to choose a "batch-type" system or choose a "continuous-type" system. The batch systems can be used in parallel or in series, operated on a cyclic basis (at prescribed residence times), be sequentially loaded, processed, and unloaded, and yield a sufficient bulk removal efficiency. The "continuous-type" systems generally refer to a number of batch vessels, operated sequentially, with the supercritical carbon dioxide gas flow and the sequential loading, processing, and unloading of the feed and product solids can be envisioned as counter current flow of the solids movement from feed to product with respect to the flow of the supercritical carbon dioxide. The directional loading, processing, and unloading is opposite to the flow of the supercritical carbon dioxide. This type of "continuous", counter current operation is generally referred to as continuous, counter current, sequencing-batch operation. Therefore, when there are one or two batch stages, in series or parallel, the term "batch" tends to be used, and when there are three or more stages, if they operate in parallel flow to the supercritical carbon dioxide, the term "batch" is also used. However, when they operate in counter current flow of the material to be extracted to the supercritical carbon dioxide, we call them counter current "sequencing-batch" simulating counter current flows of material feed and desired product to the flow direction of the supercritical carbon dioxide. It should be understood that "continuous" can also define a process in which the feed and solvent are fed continuously through a fixed system and the products are continuously removed.

When the supercritical fluid is selected as the extraction solvent, the separation of the aqueous phase from the solvent phase may occur by releasing the temperature and pressure placed upon the supercritical fluid, allowing the fluid to return to a gaseous state.

The solvents selected for the solubilization method of this invention are based upon solubility parameters and cohesion properties explained by Charles Hansen in "Hansen Solubility Parameters: A User's Handbook" by Charles M. Hansen, CRC Press (2007) and in "The CRC Handbook and Solubility Parameters and Cohesion Parameters," Edited by Allan F. M. Barton (1999). Each material is defined by three points in 3D space and these three points are known as the Hansen Solubility Parameters (HSP) which may be defined as follows.

Solubility parameters are theoretically calculated numerical constants which are a useful tool in predicting the ability of a solvent material to dissolve a particular solute. When the solubility parameters of a solvent falls within the solubility parameter range of a solute, i.e., the material to be dissolved, solubilization of the solute is likely to occur. There are three Hansen empirically- and theoretically-derived solubility parameters, a dispersion-force component ($\delta_D$), a polar or dipole interaction component ($\delta_P$) and a hydrogen-bonding component ($\delta_H$). Each of the three parameters (i.e., dispersion, polar and hydrogen bonding) represents a different characteristic of solvency, or solvent capability. In combination, the three parameters are a measure of the overall strength and selectivity of a solvent. The Total Hansen solubility parameter, which is the square root of the sum of the squares of the three parameters mentioned previously, provides a more general description of the solvency of the solvents. Individual and total Solubility Parameter units are given in $MPa^{0.5}$ or $(J/cc)^{0.5}$.

These three parameters can be treated as co-ordinates for a point in three dimensions also known as the Hansen space. The nearer two molecules are in this three dimensional space, the more likely they are to dissolve into each other. To determine if the parameters of two molecules (usually a solvent and a polymer) are within range a value called interaction radius ($R_0$) is given to the substance being dissolved. This value determines the radius of the sphere in Hansen space and its center is the three Hansen parameters. To calculate the distance (Ra) between Hansen parameters in Hansen space the following formula is used.

$$(Ra)^2 = 4(\delta_{d2}-\delta_{d1})^2 + (\delta_{p2}-\delta_{p1})^2 + (\delta_{h2}-\delta_{h1})^2$$

The Hansen solubility parameters can be calculated by "Molecular Modeling Pro" software, version 5.1.9 (ChemSW, Fairfield Calif., www.chemsw.com) or Hansen Solubility from Dynacomp Software. The solubility parameters of solvents useful herein are shown in Table 1, below.

TABLE 1

| Component | Dispersion ($\delta D$) | Polarity ($\delta P$) | Hydrogen Bonding ($\delta H$) | Ra (With Ethyl Acetate) | Ra (With Dodecanol) |
|---|---|---|---|---|---|
| ethyl acetate | 15.8 | 5.3 | 7.2 | 0 | 4.5 |
| Carbon Dioxide | 15.7 | 6.3 | 5.7 | 1.8 | 5.7 |
| hexane | 14.9 | 0 | 0 | 9.1 | 10.0 |
| heptanes | 15.3 | 0 | 0 | 9 | 10.2 |
| benzene | 18.4 | 0 | 2 | 9.1 | 11.8 |
| diethyl ether | 14.5 | 2.9 | 5.1 | 4.1 | 4.3 |
| di-n-propyl ether | 15.5 | 2.3 | 4.5 | 4.1 | 5.7 |
| methylene chloride | 18.2 | 6.3 | 6.1 | 5 | 9.4 |
| carbon tetrachloride | 17.8 | 0 | 0.6 | 9.4 | 12.0 |
| propylene Carbonate | 20 | 18 | 4.1 | 15.5 | 19.6 |

TABLE 1-continued

| Component | Dispersion ($\delta D$) | Polarity ($\delta P$) | Hydrogen Bonding ($\delta H$) | Ra (With Ethyl Acetate) | Ra (With Dodecanol) |
|---|---|---|---|---|---|
| propylene glycol methyl ether acetate | 15.6 | 5.6 | 9.8 | 2.6 | 3.9 |
| 1,1,1-trichloroethane | 16.8 | 4.3 | 2 | 5.7 | 9.2 |
| methyl nonafluorobutyl ether* | 13.74 | 3.59 | 4.14 | 5.4 | 5.2 |
| ethyl nonafluorobutyl ether* | 14.31 | 4.36 | 3.98 | 4.5 | 5.5 |

*Methyl and Ethyl Nonafluorobutyl Ethers are commercially available from TCI AMERICA, 9211 N. Harborgate Street, Portland, OR 97203, U.S.A.

Undesirable Non-Polar Material

The compositions of the present invention contain at least 0.01% of undesirable non-polar materials. In one embodiment the composition contains from about 0.01% to about 20%, by weight of the composition, of undesirable non-polar materials. In one embodiment, the composition contains from about 0.01% to about 10%, alternatively from about 0.01% to about 7%, alternatively from about 0.1% to about 5%, of undesirable non-polar materials, all by weight of the composition.

As used herein "undesirable non-polar materials" refers generally to any non-polar materials that are found in the water-soluble surfactant composition in need of treatment. In one embodiment, the undesirable non-polar materials are selected from residual alcohols, alcohol ethoxylates, aldehydes, ethers, ketones, alkylamines, amides, and esters.

In one embodiment, the undesirable non-polar materials may be off-tasting components selected from impurities, unreacted starting materials, by-products and/or contaminants. Such undesirable non-polar materials may be described by consumers as soapy, bitter, metallic, earthy or dirty, and astringent. Soapy is typically characterized by the presence of dodecanal or dodecanol. Bitter taste may occur in the presence of alkyl amines or alcohols.

In one embodiment, the water-soluble surfactant is cocoamidopropyl betaine and the composition contains at least 0.001%, by weight of the composition, alternatively from 0.005% to 20%, by weight of the composition of amine and amide materials.

In one embodiment, the water-soluble surfactant is cocoamidopropyl betaine and the composition contains at least 20% cocoamidopropyl betaine surfactant and contains at least 0.001%, alternatively from 0.005% to 20%, by weight of the composition, of amine and amide materials.

In one embodiment, the composition contains at least 0.001%, alternatively at least 0.005%, by weight of the composition, of total alcohols.

Useful in Liquid-Liquid Extraction Processes

As used herein, liquid-liquid extraction, also known as solvent extraction and partitioning, refers to a standard method to separate compounds based upon their relative solubilities in two different immiscible liquids, here, water and a solvent. It is an extraction of a substance from one liquid phase into another liquid phase. The "liquid-liquid" phrase refers to the two different immiscible liquids that are mixed as part of the extraction procedure. As used herein, immiscible refers to the ability of the two liquids to form at least two layers when mixed together. The layers may be formed after mixing the two liquids and allowing them to sit at rest for a variable period of time, or in some instances, the mixture of the two liquids may be centrifuged and/or cooled below room temperature in order to assist the separation.

Typically in liquid-liquid extraction, one of the phases will be aqueous, and the other a non-polar lipophilic organic solvent such as ether, MTBE, dichloromethane, chloroform, or ethyl acetate. Most organic solvents float on top of an aqueous phase, though important exceptions are most halogenated solvents.

Equipment typically used in a laboratory setting for liquid-liquid extraction includes a separatory funnel. In a small scale plant or lab, batch-wise liquid-liquid extraction methods may be used, such as by mixing the two liquids and then introducing them into a large scale separatory funnel. In larger scale plant production, a multistage continuous counter current extractor may be used to quickly and easily run multiple extractions in sequence. In one embodiment, the process includes the use of a machine selected from centrifugal contactors, thin layer extractors, spray columns, pulsed columns, and mixer-settlers, and combinations thereof, in the extraction process.

In many instances, a separatory funnel has the shape of a cone surmounted by a hemisphere. It has a stopper at the top and stopcock (tap), at the bottom. Separating funnels used in laboratories are typically made from borosilicate glass and their stopcocks are made from glass or PTFE. Typical sizes are between 50 mL and 3 L. In industrial chemistry they can be much bigger and for much larger volumes, centrifuges are used.

To use a separatory funnel, the extraction mixture is introduced into the separatory funnel through the top with the stopcock at the bottom closed. The funnel is then closed and shaken gently by inverting the funnel multiple times. The funnel is then inverted and the tap carefully opened to release excess vapor pressure. The separating funnel is set aside to allow for the complete separation of the phases. The top and the bottom tap are then opened and the two phases are individually released by gravitation and separately captured.

Water-Soluble Surfactant

The compositions disclosed herein contain a water-soluble surfactant and one more undesirable non-polar materials. Water-soluble surfactants in aqueous solutions containing undesirable non-polar materials that may be useful herein include those commercially available from suppliers such as Rhodia (located in Spartanburg, S.C., USA), Stepan (located in Metamoros, Mex. and Winder, Ga., USA), Croda (located in Edison, N.J., USA) and Clariant (located in Charlotte, N.C., USA.

Many commonly used water-soluble surfactant raw materials are produced by commercial suppliers as aqueous solutions at fairly high concentrations. These surfactants are good candidates for odor, color, and/or taste improvement by liquid-liquid extraction and may be used in the compositions set forth herein.

Water-soluble alkyl phosphate surfactant compositions that may be used in the compositions set forth herein include commercially available compositions shown in Table 1:

TABLE 1

| Supplier | Trade-name | Alkyl | Chain | Concentration (in aqueous solution) | Salt | EO # | Average MW |
|---|---|---|---|---|---|---|---|
| Croda | 230K | Mono | Laureth | 40% | Potassium | 0 | 266.317 |
| Rhodia | L204K | Mono | Laureth | 20% | Potassium | 0 | 266.317 |
| Rhodia | L213/S | Mono | Laureth | 30% | Sodium | 1 | 310.3712 |
| Clariant | 340D | Di | Laureth | 40% | none | 4 | 442.5305 |
| Rhodia | L130 | Mono | Laureth | 100% | none | 3 | 398.4774 |
| Rhodia | L190 | Mono | Laureth | 100% | none | 9 | 662.7968 |

Aqueous Phase

As used herein, "aqueous phase" refers to the portion of the composition herein containing water, water-soluble surfactant, and other water-soluble materials.

Solvent Phase

As used herein, "solvent phase" refers to the portion of the composition herein containing the extraction solvent, the undesirable non-polar materials, and other water-insoluble materials.

Generally, the solvent phase and the aqueous phase will be immiscible.

EXAMPLES

Example I

Composition Containing MAP L213/S Surfactant

A composition according to the present invention was made by combining MAP L213/S mono alkyl phosphate surfactant supplied by Rhodia, and containing undesirable non-polar materials and water, with ethyl acetate (supplied by Honeywell Burdick & Jackson, Muskegon, Mich., USA) as the extraction solvent.

To form the composition, 100 grams of MAP L213/S were placed into a clean 250 mL separatory funnel and 100 mL of ethyl acetate was added to the separatory funnel, which was stoppered, and shaken vigorously for 1 minute, forming a composition according to the present invention. By allowing the contents of the separatory funnel to rest for 1 hour, the composition settled into two layers, an aqueous phase and a solvent phase.

Such composition may be used in a liquid-liquid extraction process to improve the taste of the mono alkyl phosphate surfactant.

Example II

Composition Containing Cocoamidopropyl Betaine Surfactant

A composition according to the present invention was made by combining cocoamidopropyl betaine surfactant, supplied by Stepan, Mexico SA DE CV (Matamoros, Mex.), and containing undesirable non-polar materials and water, with ethyl acetate (supplied by Honeywell Burdick & Jackson, Muskegon, Mich., USA) as the extraction solvent.

To form the composition, 20 grams of cocoamidopropyl betaine surfactant were placed into a clean 250 mL separatory funnel and 20 mL of ethyl acetate was added to the separatory funnel, which was stoppered, and shaken vigorously for 1 minute, forming a composition according to the present invention. By allowing the contents of the separatory funnel to rest for 1 hour, the composition settled into two layers, an aqueous phase and a solvent phase.

Such composition may be used in a liquid-liquid extraction process to improve the taste of the cocoamidopropyl betaine surfactant.

Example III

Composition Containing Lauryl Betaine Surfactant

A composition according to the present invention was made by combining lauryl betaine surfactant, supplied by Mason Chemical Company (Arlington Heights, Ill., USA), and containing undesirable non-polar materials and water, with ethyl acetate (supplied by Honeywell Burdick & Jackson, Muskegon, Mich., USA) as the extraction solvent.

To form the composition, 100 grams of lauryl betaine surfactant were placed into a clean 250 mL separatory funnel and 100 mL of ethyl acetate was added to the separatory funnel, which was stoppered, and shaken vigorously for 1 minute, forming a composition according to the present invention. By allowing the contents of the separatory funnel to rest for 1 hour, the composition settled into two layers, an aqueous phase and a solvent phase.

Such composition may be used in a liquid-liquid extraction process to improve the taste of the lauryl betaine surfactant.

Example IV

Composition Containing Sodium Lauryl Sulfate Surfactant

A composition according to the present invention was made by combining sodium lauryl sulfate surfactant, supplied by Stepan (Winder, Ga., USA), and containing undesirable non-polar materials and water, with ethyl acetate (supplied by Honeywell Burdick & Jackson, Muskegon, Mich., USA) as the extraction solvent.

To form the composition, 100 grams of sodium lauryl sulfate surfactant were placed into a clean 250 mL separatory funnel and 100 mL of ethyl acetate was added to the separatory funnel, which was stoppered, and shaken vigorously for 1 minute, forming a composition according to the present invention. By allowing the contents of the separatory funnel to rest for 1 hour, the composition settled into two layers, an aqueous phase and a solvent phase.

Such composition may be used in a liquid-liquid extraction process to improve the taste of the sodium lauryl sulfate surfactant.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 g" is intended to mean "about 20 g." All percentages, ratios and proportions herein are on a weight basis unless otherwise indicated. Except as otherwise noted, all amounts including quantities, percentages, portions, and proportions, are not intended to indicate significant digits.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Except as otherwise noted, the articles "a", "an", and "the" mean "one or more".

As used herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A composition useful in liquid-liquid extraction processes for improving the taste of water-soluble surfactants, the composition comprising two immiscible phases:
    a. an aqueous immiscible phase comprising:
        i. from about 5% to about 90%, by weight of the composition, water;
        ii. from about 5% to about 60%, by weight of the composition, a surfactant selected from the group consisting of alkyl phosphate surfactants, alkyl phosphate ethoxylated surfactants, lauryl sulfate surfactants, betaine surfactants, amine oxide surfactants, and combinations thereof;
    b. a solvent immiscible phase comprising:
        i. from about 5% to about 90%, by weight of the composition, an extraction solvent wherein the extraction solvent is selected from solvents having individual Hansen solubility parameters of a dispersion force component ($\delta_D$) ranging from about 13 to about 19 $(MPa)^{0.5}$, a polar component $\delta(\delta_P)$ ranging from 0 to about 9 $(MPa)^{0.5}$ and a hydrogen bonding component ($\delta_H$) ranging from 0 to about 11 $(MPa)^{0.5}$;
        ii. at least about 0.01%, by weight of the composition, an undesirable non-polar material selected from the group consisting of alcohol ethoxylates, aldehydes, ethers, ketones, alkylamines, esters, dodecanol, dodecanal, and combinations thereof;

wherein the phases are immiscible;

wherein the undesirable non-polar materials are off-tasting and negative odor components selected from impurities, unreacted starting materials, by-products and contaminants.

2. The composition of claim 1 wherein the surfactant comprises cocoamidopropyl betaine.

3. The composition of claim 1 wherein the surfactant comprises mono alkyl phosphates.

4. The composition of claim 1 wherein the extraction solvent is selected from ethyl acetate, water-saturated ethyl acetate, ethyl propionate, ethyl butyrate, ethyl pentanoate, ethyl caproate, ethyl caprylate, ethyl pelargonate methyl acetate, methyl propionate, methyl butyrate, short chain esters, supercritical carbon dioxide, and mixtures thereof.

5. The composition of claim 4 wherein the extraction solvent is ethyl acetate.

6. The composition of claim 1 wherein the ratio of extraction solvent to surfactant in the composition is from about 1:10 to about 10:1.

7. The composition according to claim 1 wherein the composition further comprises a phase separation enhancer selected from the group consisting of salt, pH modifiers, and combinations thereof.

8. The composition according to claim 1 wherein the material comprises dodecanol, dodecanal, or combinations thereof.

9. The composition according to claim 1 wherein the composition further comprises a phase separation enhancer selected from the group consisting of salt, pH modifiers, and combinations thereof.

10. The composition according to claim 1 wherein the material comprises dodecanol, dodecanal, or combinations thereof.

11. A composition useful in liquid-liquid extraction processes for improving the taste of water-soluble surfactants, the composition comprising two immiscible phases:
   a. an aqueous immiscible phase comprising:
      i. from about 5% to about 90%, by weight of the composition, water;
      ii. from about 5% to about 60%, by weight of the composition, surfactant selected from the group consisting of cocoamidopropyl betaines, lauryl betaines capryl/capramidobetaines, sodium lauryl sulfates, mono alkyl phosphates, alkyl ethoxylated phosphates, amine oxides, and combinations thereof;
   b. a solvent immiscible phase comprising:
      i. from about 5% to about 90%, by weight of the composition, extraction solvent selected from the group consisting of ethyl acetate, water-saturated ethyl acetate, ethyl propionate, ethyl butyrate, ethyl pentanoate, ethyl caproate, ethyl caprylate, ethyl pelargonate methyl acetate, methyl propionate, methyl butyrate, short chain esters, and combinations thereof;
      ii. at least about 0.01%, by weight of the composition, an undesirable non-polar material selected from the group consisting of alcohol ethoxylates, aldehydes, ethers, ketones, alkylamines, esters, dodecanol, dodecanal, and combinations thereof;

wherein the phases are immiscible;

wherein the undesirable non-polar materials are off-tasting and negative odor components selected from impurities, unreacted starting materials, by-products and contaminants.

12. The composition of claim 11 wherein the surfactant comprises cocoamidopropyl betaine.

13. The composition of claim 11 wherein the surfactant comprises mono alkyl phosphates.

14. The composition of claim 11 wherein the extraction solvent is ethyl acetate.

15. The composition of claim 11 wherein the ratio of extraction solvent to surfactant in the composition is from about 1:10 to about 10:1.

16. The composition according to claim 11 wherein the composition further comprises a phase separation enhancer selected from the group consisting of salt, pH modifiers, and combinations thereof.

17. The composition according to claim 11 wherein the material comprises dodecanol, dodecanal, or combinations thereof.

18. A composition useful in liquid-liquid extraction processes for improving the taste of water-soluble surfactants, the composition comprising two immiscible phases:
   a. an aqueous immiscible phase comprising:
      i. from about 5% to about 90%, by weight of the composition, water;
      ii. from about 5% to about 60%, by weight of the composition, a mono alkyl phosphate surfactant;
   b. a solvent immiscible phase comprising:
      i. from about 5% to about 90%, by weight of the composition, an extraction solvent selected from the group consisting of ethyl acetate, food grade ethyl esters, and combinations thereof;
      ii. at least about 0.01%, by weight of the composition, an undesirable non-polar material selected from the group consisting of alcohol ethoxylates, aldehydes, ethers, ketones, alkylamines, esters, dodecanol, dodecanal, and combinations thereof;

wherein the phases are immiscible;

wherein the undesirable non-polar materials are off-tasting and negative odor components selected from impurities, unreacted starting materials, by-products and contaminants.

19. The composition of claim 18 wherein the extraction solvent is ethyl acetate.

20. The composition of claim 18 wherein the ratio of extraction solvent to surfactant in the composition is from about 1:10 to about 10:1.

* * * * *